(12) United States Patent
Minor

(10) Patent No.: US 7,072,806 B2
(45) Date of Patent: Jul. 4, 2006

(54) METHODS AND SYSTEM FOR COMPARING DATA VALUES ACROSS MULTIPLE PLATFORMS

(75) Inventor: James M. Minor, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/169,991

(22) Filed: Jun. 28, 2005

(65) Prior Publication Data

US 2006/0004523 A1 Jan. 5, 2006

Related U.S. Application Data

(63) Continuation of application No. 10/737,320, filed on Dec. 16, 2003, now Pat. No. 6,985,834.

(51) Int. Cl.
*G06F 15/00* (2006.01)

(52) U.S. Cl. ...................................... 702/196; 702/182

(58) Field of Classification Search .................. 702/22, 702/29, 30, 32, 86, 182, 186, 196; 435/6, 435/91.1

See application file for complete search history.

(56) References Cited

U.S. PATENT DOCUMENTS

| | | | |
|---|---|---|---|
| 5,860,917 A | 1/1999 | Comanor et al. | |
| 5,948,902 A | 9/1999 | Honkanen et al. | |
| 6,171,797 B1 | 1/2001 | Perbost | |
| 6,180,351 B1 | 1/2001 | Cattell | |
| 6,188,969 B1 | 2/2001 | Minor | |
| 6,221,583 B1 | 4/2001 | Kayyem et al. | |
| 6,222,664 B1 | 4/2001 | Dorsel | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,355,921 B1 | 3/2002 | Staton et al. | |
| 6,371,370 B1 | 4/2002 | Sadler et al. | |
| 6,406,849 B1 | 6/2002 | Dorsel et al. | |
| 6,486,457 B1 | 11/2002 | Dorsel et al. | |
| 6,518,556 B1 | 2/2003 | Staton et al. | |
| 6,792,071 B1* | 9/2004 | Dewaele ...................... | 378/62 |
| 2003/0160183 A1 | 8/2003 | Dorsel et al. | |

OTHER PUBLICATIONS

Yuan et al., "Multiple Imputation for Missing Data: Concepts and New Development" and Abstract, SAS Institute Inc., Rockville, MD, 2000.

"Software for Multiple Imputation", http://www.stat.psu.edu/jls/misoftwa.html, downloaded Oct. 3, 2003.

"Multiple Imputation for Missing Data", http://support.sas.com/md/app/da/new/dami.html, undated, downloaded Oct. 3, 2003.

(Continued)

*Primary Examiner*—Bryan Bui

(57) ABSTRACT

Methods, systems and computer readable media for imposing monotonic consistency among results of multiple platforms measuring the same specific property for the same/equivalent series of samples, to provide viable comparisons of sensitivity and precision among the platforms as well as provide useful conversion formulas among the platforms to ensure equivalent quantitation.

9 Claims, 6 Drawing Sheets

| | $P_1$ | $P_2$ | $P_3$ | $\overline{P}$ |
|---|---|---|---|---|
| $0.25\, b_2$ | $\times_1$ | $\blacktriangle_1$ | $\bullet_1$ | $\blacksquare_1$ |
| $0.5\, b_2$ | $\times_2$ | $\blacktriangle_2$ | $\bullet_2$ | $\blacksquare_2$ |
| $b_1$ | $\times_3$ | $\blacktriangle_3$ | $\bullet_3$ | $\blacksquare_3$ |
| $b_2$ | $\times_4$ | $\blacktriangle_4$ | $\bullet_4$ | $\blacksquare_4$ |

200

OTHER PUBLICATIONS

"Introducing does/response curves", http://graphpad.com/curvefit/introduction89.htm, undated, downloaded Oct. 21, 2003.

"Total Lease Squares and Error-in-Variables Modeling", edited by Van Huffel and Lemmerling, http://www.wkap.n1/prod/b/1-4020-0476-1, Feb., 2002.

"Probability and Statistics", http://www.mathpages.com/home/iprobabi.htm, downloaded Oct. 20, 2003.

"Perpendicular Regression of a Line", http://www.mathpages.com/home/kmath110.htm, downloaded Oct. 20, 2003.

* cited by examiner

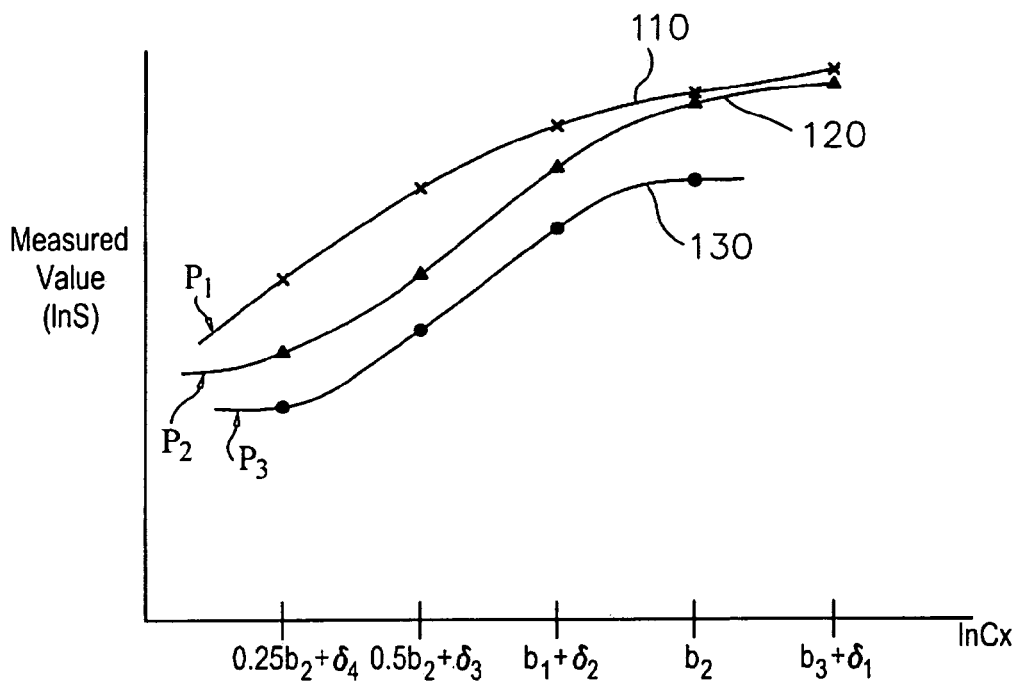

FIG. 1

|  | $P_1$ | $P_2$ | $P_3$ | $\overline{P}$ |
|---|---|---|---|---|
| $0.25\,b_2$ | $\times_1$ | $\blacktriangle_1$ | $\bullet_1$ | $\blacksquare_1$ |
| $0.5\,b_2$ | $\times_2$ | $\blacktriangle_2$ | $\bullet_2$ | $\blacksquare_2$ |
| $b_1$ | $\times_3$ | $\blacktriangle_3$ | $\bullet_3$ | $\blacksquare_3$ |
| $b_2$ | $\times_4$ | $\blacktriangle_4$ | $\bullet_4$ | $\blacksquare_4$ |

FIG. 2
200

|  | $P_1$ | $P_2$ | $P_3$ | $P_4$ | $P_5$ |
|---|---|---|---|---|---|
| $b_1$ | $P_{11}$ | $P_{21}$ | $P_{31}$ | — | $P_{51}$ |
| $b_2$ | $P_{12}$ | — | $P_{32}$ | — | $P_{52}$ |
| $b_3$ | $P_{13}$ | $P_{23}$ | $P_{33}$ | $P_{43}$ | $P_{53}$ |
| $b_4$ | — | $P_{24}$ | $P_{34}$ | $P_{44}$ | $P_{54}$ |
| $b_5$ | $P_{15}$ | $P_{25}$ | $P_{35}$ | $P_{45}$ | $P_{55}$ |

FIG. 3
300

METHODS AND SYSTEM FOR COMPARING DATA VALUES ACROSS MULTIPLE PLATFORMS

This application is a continuation of application Ser. No. 10/737,320, filed Dec. 16, 2003, now U.S. Pat. No. 6,985,834, which is hereby incorporated herein, in its entirety, by reference thereto, and to which application we claim priority under 35 USC §120.

FIELD OF THE INVENTION

The present invention relates to the field of data quantitation, and more particularly to quantitation of biological data.

BACKGROUND OF THE INVENTION

Many assays and related tests quantify a physical property of a sample by comparing a measured assay value against an assay curve for the physical property of interest. For example, a blood sample may contain some initially unknown level of a particular pathogen. When the sample is evaluated with an assay for the pathogen of interest, it provides a measurable signal that tends to be monotonically changing according to (and typically somewhat proportional to, at least in a log—log representation) the pathogen level in the patient's blood.

Examples of measured signals include luminescence or radiation emitted from a test sample, PCR-based methods, the absorption coefficient of the sample, the color of a sample, etc. These different ways or platforms for measuring the same quantity are not easily usable together as they do not quantify to the same scale. For comparing and combining phenomenological information and observations, researchers have needs for easily converting measurements taken by one platform to the scale used by another platform. For example, a researched may need to integrate data comprising measurements taken on a luminescence platform with those taken on a radiation platform. Even measurements taken with similar platforms, such as a single channel microarray versus a dual channel microarray need to be converted in order to be usable together. Thus there is a need for improved methods and tools for normalizing data from different platforms so that they are based upon the same scale.

In a typical case, the assay procedure involves contacting a test sample (analyte) with a test solution followed by a washing step. Thereafter, the test quantity of interest is measured and compared against an assay curve (sometimes referred to as a "response curve"). The assay curve provides the measured value as a dependent variable and the "true value" (that is unknown, but approximate) of the property of interest as an independent variable. In one specific example, an assayed sample of hepatitis B virus (HBV) DNA emits light of a luminescence that varies with viral load. Thus, the luminescence of the sample is detected and compared against the assay curve that specifies a corresponding value of viral load for the sample.

In most useful assays, the assay curve increases monotonically with the property of interest over the dynamic range (e.g., luminescence increases monotonically with viral load). Often the assay is designed so that the response of the assay is nearly linear over a specific dynamic range. To achieve this, the assay curve may be expressed as the logarithm of the measured value versus the logarithm of the property value. In practice, however, such assay curves rarely assume a truly linear form. Frequently, there is a slight curvature over the dynamic range which can be better represented by a quadratic expression. Further, near or just beyond the limits of the specific dynamic range, the response curve often flattens (i.e., the measured value changes only slightly with respect to changes in the true property value) to give the overall response curve, essentially a "sigmoid" shape.

Even with widely used and validated assays, one is never certain that the specified property value for a sample is truly accurate. For example, the calibration of an assay may be inaccurate because the "standard" used to generate the assay curve is itself inaccurate. Sometimes, the property value of a standard changes slightly with time. And sometimes when a standard runs out, the new standard created to replace the old does not possess the same true property value as the old standard. Further, while a given assay may be internally consistent over a period of time, it is still very difficult or impossible to accurately correlate two different assays for the same analyte.

Many applications could benefit from improved confidence in measurements of the property value consistent across assays. For example, one might want to use two or more different assays to monitor the same property value. A hepatitis B patient may have had his viral load monitored with a first assay that becomes temporarily unavailable. When a second assay—which relies on an entirely different physical mechanism than the first assay—is used in place of the first and gives a rather high reading of viral load, it could mean either (a) the patient's viral load is truly increasing or (b) the second assay employs an assay curve that, in comparison to the first assay's curve, gives a higher property value reading for a given sample. Obviously, an attending health care professional needs a reliable value consistent with both assays.

Also, parametric models for predicting the outcome of a medical treatment or other course of action are created from prognostic variables relevant to the models (e.g., assay results). The accuracy of the model is improved as more-consistent data is used to construct it. If that data is provided as assay results for two or more assays, there must be some way to establish a conversion between the assay results of the two or more assays. Otherwise the resulting model may fail to accurately handle inputs from one or more of the assays used to construct the model.

Other applications exist that require a conversion between property values specified by multiple assays or methods. For example, when an enterprise generates a new assay standard it must accurately correlate that standard's property value to the old standard's property value. Otherwise, assays using the new standard will not be consistent with the same assays using the old standard.

In another example, enterprises may need to compare two assays' performance (e.g., sensitivity and responsiveness) when those assays are designed to quantitate the same analyte. Several commercial assays are available for HBV DNA quantification, and laboratory managers need tools to assess how well the various assays operate. Even when results are reported in the same unit of quantification for a given sample, different assays report different results. Thus, the person conducting the comparison must ensure that the response curves of the two assays can be plotted on the same independent variable axis (the true property value axis).

Traditionally, when comparing multiple assays or batches of a standard, one uses a regression analysis to quantify the associations of interest. For example, for a series of samples, the measured values of a first assay or batch is provided as the independent variable and the measured values of the second assay or batch is provided as the dependent variable. Then one assumes a relationship between the independent and dependent variables (e.g., a linear or quadratic relationship) and a regression analysis is performed to identify parameters of the relationship that nicely fit the data. Unfortunately, linear regression analysis is restricted to comparison of only two assays at a time. Still further, this application of regression tends to violate a primary assumption for correct inference of results, i.e., the independent variable is assumed to be more precise versus the dependent variable. See e.g., Yonathan Bard, "Nonlinear Parametric Estimation," Academic Press, New York, N.Y., 1974. Hence, the more precise variable must be the independent regression variable, typically denoted as x, while the noisier variable must be the dependent or response variable, denoted y. In many assay comparisons, where one assay is selected to be y variable and the other x variable, the results are questionable since the assay errors are comparable or, worse, the x variable error is larger than the y variable error.

Hence, there is a need to compare multiple assays (or other methods) or batches of standard without the inherent bias of linear regression, to be able to convert values between the different assays or standards, and to provide a property basis consistent across all assays.

SUMMARY OF THE INVENTION

Methods, systems and recordable media for imposing monotonic consistency among results of multiple platforms measuring the same specific property for the same/equivalent series of samples in order to provide useful conversion formulas among the platforms to ensure equivalent quantitation.

Viable comparisons of sensitivity and precision among the platforms may also be provided.

A scaled index may be assigned to each sample that is more closely related to the measured property in order to enable such comparisons and conversions.

If values are missing or invalid as reported by any of the platforms, such missing or invalid values are processed to impute values to replace the missing or invalid values.

Signals from individuals platforms may be organized as a vector, and every sample may be processed in the same way to create such vectors composed of respective platforms. A virtual platform may then be calculated with corresponding value positions containing ensemble values representative of the measurement values of all platforms vectors at the corresponding positions. Ordering and scaling enabled by the ensemble values in the virtual platform may then be performed for all vectors.

Surrogate values may be constructed to represent the true values of the properties being measured, to provide consensus-correct ordering of the multi-platform vectors. A function f may be solved for, by regressing against s using an appropriate functional form such that $f_j$, for j=1 to n, is a monotonic, non-constant function of s, preferably an increasing function of s.

The quantitative regions of data for each platform may be linearized, as provided for.

Missing values may be imputed by an iterative univariate regression procedure.

These and other advantages and features of the invention will become apparent to those persons skilled in the art upon reading the details of the invention as more fully described below.

BRIEF DESCRIPTION OF THE DRAWINGS

FIG. 1 shows a graph of hypothetical data indicating the response of three separate measurement methods.

FIG. 2 shows another approach to solving the problem of converting measurements from one platform to another in terms of row vectors.

FIG. 3 shows a matrix of row vectors used in applying the approach of FIG. 2, and in which missing measurements are present.

DETAILED DESCRIPTION OF THE INVENTION

Figure 4:
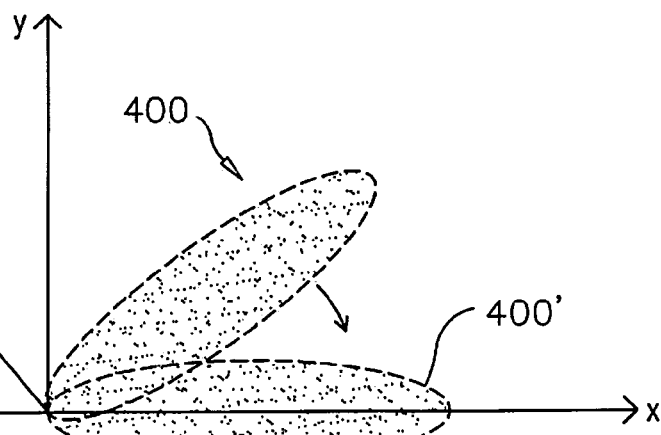
FIG. 4 is a schematic representation showing all of the values, of three platforms being compared, having been plotted in n-dimensional space, where n=3 in this example.

Before the present techniques and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the platform" includes reference to one or more platforms and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

In the present application, unless a contrary intention appears, the following terms refer to the indicated characteristics.

A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another.

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948, 902 and references cited therein (all of which are incorporated herein by reference), regardless of the source.

An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", "microarray" or "bioarray", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other).

An "array layout" refers to one or more characteristics of the features, such as feature positioning on the substrate, one or more feature dimensions, and an indication of a moiety at a given location. "Hybridizing" and "binding", with respect to polynucleotides, are used interchangeably. A "pulse jet" is a device which can dispense drops in the formation of an array. Pulse jets operate by delivering a pulse of pressure to liquid adjacent an outlet or orifice such that a drop will be dispensed therefrom (for example, by a piezoelectric or thermoelectric element positioned in a same chamber as the orifice).

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "platform" refers to a system, device or process for measuring specific properties of a specified target phenomenon. Examples of platforms include, but are not limited to Versant HCV RNA qualitative and quantitative assays (Bayer Diagnostics, Berkeley, Calif.), Bayer HBV Branched-DNA (bDNA) Assay (Bayer Diagnostics, Berkeley, Calif.), Chiron Quantiplex Branched-DNA Assay (Chiron Corporation, Emeryville, Calif.), Amplicor HBV Monitor® (Roche Diagnostics, Basel, Switzerland), HC II HBV Test (Digene Corporation, Gaithersburg, Md.), Affymetrix@, GeneChip@ microarrays (Affymetrix, Santa Clara, Calif.), Agilent Oligo and DNA microarrays (Agilent Technologies, Inc., Palo Alto, Calif.), Incyte cDNA microarrays (Incyte Corporation, Palo Alto, Calif.), Amersham Lucidea™ microarrays (Amersham Biosciences Corp., Buckinghamshire, England), and Amersham CodeLink™ bioarrays (Amersham Biosciences Corp., Buckinghamshire, England A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Reference to a singular item, includes the possibility that there are plural of the same items present.

"May" means optionally.

Methods recited herein may be carried out in any order of the recited events which is logically possible, as well as the recited order of events.

A "subarray" or "subgrid" is a subset of an array. Typically, a number of subgrids are laid out on a single slide and are separated by a greater spacing than the spacing that separates features or spots or dots.

Any given substrate may carry one, two, four or more arrays or subarrays disposed on a front surface of the substrate. Depending upon the use, any or all of the arrays/subarrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features), each feature typically being of a homogeneous composition within the feature. Interfeature areas (e.g., background) will typically (but not essentially) be present which do not carry any polynucleotide (or other biopolymer or chemical moiety of a type of which the features are composed). Such interfeature areas/background typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents. Further, "in-situ" synthesis methods may be employed for fabricating biopolymer arrays, as already described above.

Following receipt by a user of an array made by any of the techniques described above, it will typically be exposed to a sample (for example, a fluorescently labeled polynucleotide or protein containing sample) and the array then read. Reading of the array may be accomplished by illuminating the array and reading the location and intensity of resulting fluorescence at multiple regions on each feature of the array. For example, a scanner may be used for this purpose which is similar to the AGILENT MICROARRAY SCANNER manufactured by Agilent Technologies, Palo Alto, Calif. Other suitable apparatus and methods are described in U.S. Publication Number "20030160183, titled Reading Dry Chemical Arrays Through The Substrate" by Dorsel et al.; and in U.S. Pat. Nos. 6,518,556; 6,486,457; 6,406,849; 6,371,370; 6,355,921; 6,320,196; 6,251,685; and 6,222,664. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,251,685, 6,221,583 and elsewhere). A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

FIG. 1 shows a graph of hypothetical data indicating the response of three separate measurement methods, and exemplifying a previous method of the present inventor, for correcting assigned values of "truth" or bottle values of prepared samples indicating how much of a measured quantity each bottle supposedly contains, i.e., a mathematically, scaled, ordered index assigned to samples. This method is described in detail in U.S. Pat. No. 6,188,969, which is incorporated herein, in its entirety, by reference thereto. The y-axis (vertical axis) represents the value of the measured quantities for each of the measurement methods (e.g., ln of the signal output "ln S" by the particular platform in response to measuring the contents of a bottle). Because these methods may employ different measurement quantities (e.g., luminescence in one case and absorptivity in another case and radioactivity in yet another case), the y-axis normally encompasses multiple units that have an arbitrary relation to one another. Typically the relation is chosen so that all response curves can be viewed together (e.g., log measurement). The x-axis (the horizontal axis) represents the value of the underlying physical property which is being measured (in this case, bottle values $b_1, b_2, b_3 \ldots$). This axis will, of course, present only a single type of units (e.g., concentration of viral DNA) and will be consistent from method to method. In the example shown, the x axis value is ln Cx, or the natural logarithm of the concentration of a virus (copies of virus per milliliter of serum), i.e., "viral load". For many applications, the absolute magnitudes of the units on the x-axis need not be known because the techniques of this invention are merely making the multiple measurement methods internally consistent with respect to the underlying physical property. Even in the case where bottle values are provided, the values may be assigned by consensus, or committee, and in some cases may be inaccurate, sometimes by as much as 30%.

By measuring the various samples containing "specified" bottle values, smooth quantitation curves 110, 120 and 130 are fitted through the measured data points (indicated by x's in curve 110, triangles in curve 120 and dots in curve 130). The smooth curves are generally defined as sigmoidal curves over a full range, although over a sub-range they may appear as a linear or as a second order curve. Curve 130 shows a full range curve with the classic sigmoidal shape. The central portion of the curve is fairly linear, which is where measurements are most reliable. The bottom "s-portion" is where this measurement platform is outside its range of reliability, where the concentration is too low to perform an accurate measurement. The top "s-portion" is where the platform becomes saturated and also cannot provide a reliable reading. The method of U.S. Pat. No. 6,188,969 optimizes the fit of the smooth curves 110, 120 and 130, by adjusting the values on the x axis (i.e., the distances between each value), by solving for correction values (e.g., $\delta_1, \delta_2, \delta_3,$ and $\delta_4$ in the example shown), thereby, at the same time, correcting the monotonically-smoothed relative values among the samples on the x axis. Since a true accurate value is not known to facilitate exact positioning of all measurements on the x-axis, a viable position "anchor value" may be chosen, arbitrarily or otherwise, against which all of the other adjustments are made. In FIG. 1, the anchor value chosen was for bottle value $b_2$.

Relative performance of the platforms may be determined both by relative sensitivity (relative steepness} of the curves and by relative scatter about such curves. If replicates of the measurements are performed, the replicate plots form "clouds," about the points shown in FIG. 1 for which replicates were run. The relative patterns of these clouds can be used to show relative precision of the platforms.

Dilutions of the bottle sample may also be run against the bottle samples provided. This is shown in FIG. 1 where bottle sample b2 was diluted by half (0.5b2) and then half again (0.25 $b_2$). This makes the method even more powerful, because it is known that the relative order of $0.25b_2, 0.5b_2$ and $b_2$ is accurate. Thus, even if the ordering of $b_1$ and $b_2$, for example is inaccurate and needs to be reordered, the entire sequence of $0.25b_2, 0.5b_2$ and $b_2$ is shifted as a unit when fitting to the curves.

FIG. 2 shows another approach to solving the problem of converting measurements from one platform to another. This approach uses a tabular form, where the readings shown in FIG. 1 are plotted in a chart or matrix 200 for each of three platforms $P_1, P_2$ and $P_3$. If all the data is present, as it is in the example of FIG. 2, the problem is fairly easy to solve. The goal is to assign values to the bottle values 0.25 $b_2$, $0.5b_2$, $b_1$ and $b_2$. The initial values are given by the bottle values assigned to these concentrations (or easily calculated in the case of the dilutions). Correction values ($\delta$'s, i.e. "deltas") can be assigned by an alternate method to using the Marquardt-Levenburg approach of U.S. Pat. No. 6,188,969. Using this alternate method, one may sort the profiles (rows) in matrix 200 and scale them, so that, on average, the values in the profiles are spaced correctly. One approach is to average the row values, indicated under platform $\overline{P}$, which is also referred to as a "virtual platform". This reduces random error (e.g., one reading may be low and one may be high). The average values are then sorted to put them into the right order and scaled, so that they are spaced correctly relative to each other (as was done by shifting the values along the x-axis in the example of FIG. 1). However, missing measurements due primarily to range differences among various platforms and misfortune within platforms can severely compromise such simple methods.

In this example, the initial values (bottle values) are not even necessary to solving the problem, because the ordering and scaling is done by consensus of the measured signals, i.e., the values in the matrix 200. That is, surrogates to bottle values (called the "s" values) are constructed. The "s" values provide consensus-correct ordering of all multi-measurement vectors (e.g., the row vectors in matrix 200). The "s" values may be used in place of bottle values to initiate another cross-platform procedure, such as the multi-measurement method described in U.S. Pat. No. 6,188,969 and referred to briefly with regard to FIG. 1 above, to improve the scaling of "s".

The measurements from all platforms (e.g., P1, P2 and P3 in FIG. 2) produce a vector with regard to each sample/concentration measured, as embodied by the rows in matrix 200 of FIG. 2. The ordering and scaling of a set of such vectors, relative to each other, by a derived index enables cross-platform comparisons. The index values of the derived index ("s" indices) represent quantitation values of discrete samples from "s". These "s" indices may be estimated for each vector by an ensemble value (i.e., mean, median, biweight, sorted rank, etc.) of values of each platform, wherein each vector value is replaced by the ensemble expected value in the sorted list of values for each platform. Unfortunately missing data can compromise this process by creating gaps and shifts in the ensemble estimates. Hence imputational methods are implemented to address occurrences of missing data.

Derivation of "s" Values

Proof that a non-singular solution of the conversion problem using "s" values as described above, follows:

Assume a vector function $f$ in n-space, where n=the number of independent platforms such that $$\frac{\partial f_j}{\partial x_k} > 0, j = 1, \ldots, n; k = 1, \ldots, n \qquad (1)$$

and where x is closely related to the target property that is desired to be quantitated or measured.

$$\frac{\partial f_k}{\partial x_k} = 1 \qquad (2)$$

Without loss of generality, let $$f_k = x_k \qquad (3)$$

Note that the vector function $f$ includes a conversion from any platform to any other platform, and the cross-platform partial derivative of $f_j$ relative to $f_k$ directly estimates relative sensitivity between platforms j and k. The signal-cloud (such as formed by replicates and/or adjacent positions on the x-axis due to pseudo-replicates) projected to dimensions j and k (i.e., a particular platform comparison) gives direct information on relative precision between j and k.

The assumptions imply that there exists a scalar one-to-one function "s" such that $$\frac{\partial s}{\partial x_k} > 0, k = 1, \ldots, n \quad (4)$$

$$\text{e.g., } s = \sum_{j=1}^{n} c_j f_j, c_j \geq 0, j = 1, \ldots, n \quad (5)$$

Hence, for a given value of s, all platforms ($f_j$, j=1, ..., n) have a unique value. In practice, $f_j$ for each j=1, ..., n will be a monotonic, non-constant function of s, preferably an increasing function of s, although monotonic, decreasing functions are possible for inverse relationships with s.

When all data values are present, such as in the case of matrix 200 in the example of FIG. 2, this method is fairly straight forward and easy to solve for the s values, and ultimately for converting from one platform to another. However, it is often the case that some data values are distorted by noise and/or data values are missing, forming an incomplete matrix. FIG. 1 gives some insight as to one cause of missing values. The dynamic ranges of all platforms are not always equal. For example, platform $P_3$ is beyond its saturation level for the measurement of bottle value $b_3$ in FIG. 1. Thus, if bottle value $b_3$ were included in matrix 200 in the example shown in FIG. 2, there would be a missing data value or some kind of message indicating that a value could not be read with regard to platform $P_3$. Other causes include complications that may arise during the measurement processes, where for one reason or another, a measurement is not able to be made for one or more sample. Thus omissions and noise occur even when all the platforms have the same dynamic range, e.g. multiple channels of microarray measurements, or measuring replicates on the same platform, wherein each group of replicate measurements is referred to as a distinct platform.

Noise and missing measurements compromise the efficacy of this method. To correct for noise and missing values (missing measurements), imputational methods are applied to insert most-likely expected values into the missing value positions, such as those shown by the horizontal line in matrix 300 of FIG. 3. One approach is to use manual imputation where appropriate. For example, going back again to FIG. 1, if the matrix approach were used for the data shown there, the missing value for platform $P_3$ with regard to bottle value $b_3$ may be a good candidate for manual imputation, where the value read by platform $P_3$ for bottle value $b_2$ could be inserted. This could be a good choice for a manual imputation value, since the value for $b_2$ is already in the saturation part of the sigmoidal curve for platform $P_3$, so the value for b3, if it could be read, would also be substantially equal to the value for $b_2$ (i.e., the upper limit value for platform $P_3$).

It should be noted here that the purpose of imputation is not to replace missing information or missing values, but to insert estimates for missing values that will have minimal impact on the analysis method regarding the values that are not missing. So the goal of imputation is not to put in the true value that is missing, but to insert a value that will have minimal effect upon the analysis of the good data values that are not missing. In this way, a profile of a large number of data values that is missing only one or two data values need not be discarded from an analysis. The goal of imputation is to enable the use of such profiles, such that the benefits of the imputation far outweigh the negative consequences of the imputed values.

Another approach to imputation is through the use of sophisticated multi-variate imputation. For example, expected values may be estimated by "errors-in-variables" regression or matrix-reduction procedures. Such expectation values may be generated by using the regression and imputation iterations as taught in co-pending, commonly assigned application Ser. No. 10/400,372 filed Mar. 27, 2003 and titled "Method and System for Predicting Multi-Variable Outcomes", or in U.S. Pat. No. 5,860,917, applied to inverse sigmoidal transforms (linearizations) of the original log measurements for each platform. Another option is to use matrix-reduction functional smoothing as taught in the preceding references. For example, each platform can be regressed on all other platforms with imputation updates until convergence. Both U.S. application Ser. No. 10/400,372 and U.S. Pat. No. 5,860,917 are incorporated herein, in their entireties, by reference thereto. Other forms of imputation may also be used. For example, an interpolation of values, based on surrounding rows and columns of data values may be performed to impute an expectation value where a data value is missing. Further optional multiple imputation methods are described in "Multiple Imputation for Missing Data", http://support.sas.com/rnd/app/da/new/dami.html; "Software for Multiple Imputation", http://www.stat.psu.edu/~jls/misoftwa.html; and Yuan, "Multiple Imputation for Missing Data: Concepts and New Development", SAS Institute Inc., Rockville, Md.; each of which is incorporated herein, in its entirety, by reference thereto.

A determination can be made as to whether the missing value in a row profile is missing because it is outside of the dynamic range of the platform, or because of some other reason (but the value is inside the operational (dynamic) range of the platform), based upon all the non-missing values in the row profile. The range of each platform is defined by the maximum and minimum asymptotic signals of each's signal distribution. The maximum signal or mean of low "constant" signals (i.e., the mean signal does not change with analyte levels) of low "constant" signals, together with the minimum signal or means of high "constant" signals, may be used as estimates of the quantitation range of a platform.

Also, information may be provided by the manufacturer of the platform as to the operational/dynamic range of the platform, and this information may be applied to determine whether or not a missing value is missing because it is out of the quantitation and/or operational range of the platform. If it is determined that the missing value is outside the quantitation and/or operational range of the platform, then the expected constant asymptotic signal value may be manually imputed, as described above. If, on the other hand, it is determined that the missing value is not outside the operational range of the platform, then multi-variate imputations methods, such as described above for example, should be used to estimate a viable signal for the platform.

The "s" values are formed by combining consensus values, as described above, based on most-likely expected values for every platform, i.e., to form the virtual array. These "s" values mutually align all vectors of platforms. Conversion formulae, as well as platform comparisons may be derived by fitting an appropriate function of "s" to each vector component (each platform) of original data. A typical function used is a logistic function based on log signal versus log analyte concentration.

The "errors-in-variables" approach is generally considered a violation of basic regression assumptions. The "errors in variables" approach considers that the error in the matrix with missing values and noise is directional, not unidirectional as is generally assumed by regression and least squares modeling. By designation of appropriate data, the present method assumes a set of samples with adequate leverage to estimate shape factors for each component of the virtual platform, where vector $f$ quantitates this virtual platform. In this way, all that is required is to maximize consistency among all platforms to optimally determine this "virtual" $f$. In order to directly relate platforms, samples are required in which some of the platforms are simultaneously quantitative, such that linkage of the ensemble platform spans the domain of all possible samples. Note $f$ spans the range covered by all platforms as typically a logistic function, i.e., a virtual "super platform". This virtual platform spans the domain of analyte concentrations as defined by all the platforms as a single monotonic dose-response type function. Hence, it becomes "s" as the most direct representation of ln (analyte concentration). In case of one or more major gaps not bridged by any assay measurements, the respective "s" groups can be merged to form a single merged "s" scale that spans the total range of data.

For illustration, FIG. 4 is a schematic representation where all of the values of three of the platforms have been plotted in three-dimensional space out of n, where n=the number of platforms being analyzed. An ellipsoid 400 can be formulated using eigen-analysis, after which the data points within ellipsoid 400 may be corrected to fall along the major axis of the ellipsoid using techniques described in co-pending commonly owned application Ser. No. 10/422,570 filed Apr. 23, 2003 and titled "Microarray Performance Management System". application Ser. No. 10/422,570 is incorporated herein, in its entirety, by reference thereto.

Figure 5:
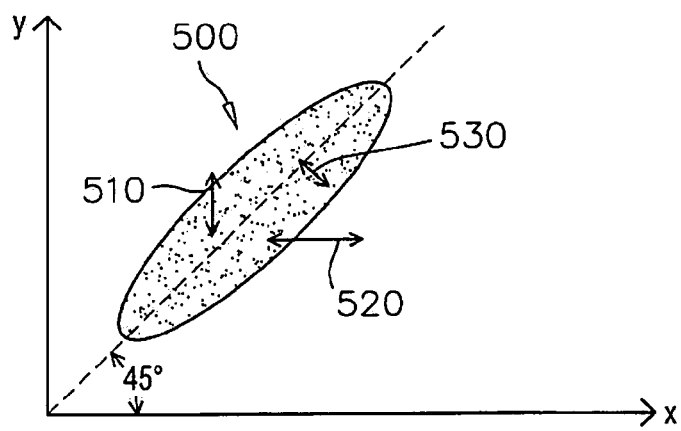
FIG. 5 illustrates a two-dimensional approach to error correction of an ellipsoid.

Stepping back for a moment, and referring to FIG. 5, a two-dimensional approach to error correction of an ellipsoid is discussed, where correction is carried out as-is, i.e., without transformations. Using the methods discussed in application Ser. No. 10/422,570, ellipsoid 500 is normalized such that its center or major axis falls along the positive diagonal (45 degrees) between the axes x and y. The correction of error that is performed to normalize the ellipsoid 500 is dependent upon the direction of error. For example, if the data points in ellipsoid 500 are plotted from a two-channel microarray and the channel plotted on the x-axis is a reference, the reference is assumed to be error free. In this case, the direction of error correction would be parallel to the y axis, such as shown by arrow 510 in FIG. 5. That is, each of the data points would be shifted along the vertical axis (parallel to y axis and orthogonal to x axis) to shift the ellipsoid so that it aligns with the diagonal. This is the basic assumption of statistical regression of y on x. Likewise, if the y axis plots a reference channel or other error-free channel, the direction of error correction would be in the direction of arrow 520, orthogonal to the y-axis This is the basic assumption of statistical regression of x on y. However, if both channels are experimental data channels and are assumed to have about the same amount of error, the direction of error correction would be normal to the main diagonal, as indicated by arrow 530. If the relative sizes of the errors are known for each channel, then the angle of the error correction direction may be adjusted proportionally.

Missing values are imputed such that the plot of the completed data point (vector) falls directly on the principal axis.

This same approach can be used for an ellipsoid plotted in high dimensional space, which cannot be visualized. However, the point is that the process represented by FIG. 4 is not restricted to three dimensions. That is, the ellipsoid 400 may be normalized so that the major axis of ellipsoid falls on the positive quadrant diagonal. The error is corrected in the direction of the vector error. Alternatively, a mathematical theory of the present inventor holds that when there are errors in both the x and y directions, for a two-dimensional ellipsoidal plot, the bias caused by a fit of one variable (x or y) to the other (y or x), both with comparable error, can be reduced by weighting the residual sum of squares of y regressed on x by the reciprocal of the functional gradient of the y axis of the plotted ellipsoid with respect to the x variable. To eliminate the need for bias-weighting, ellipsoid 400 is generated by eigen-analysis, and then rotated to the nearest axis (see rotated ellipsoid 400'), by a rotation transformation in n-dimensional space to reduce the gradient to zero, so that the bias is zero. The data points in the ellipsoid are then corrected by functional fitting according to a density profile, so that no bias effect occurs. The corrected ellipsoid is then rotated back to the positive quadrant diagonal. Note that only the noisy channels need be processed according to the foregoing technique.

Figure 6:
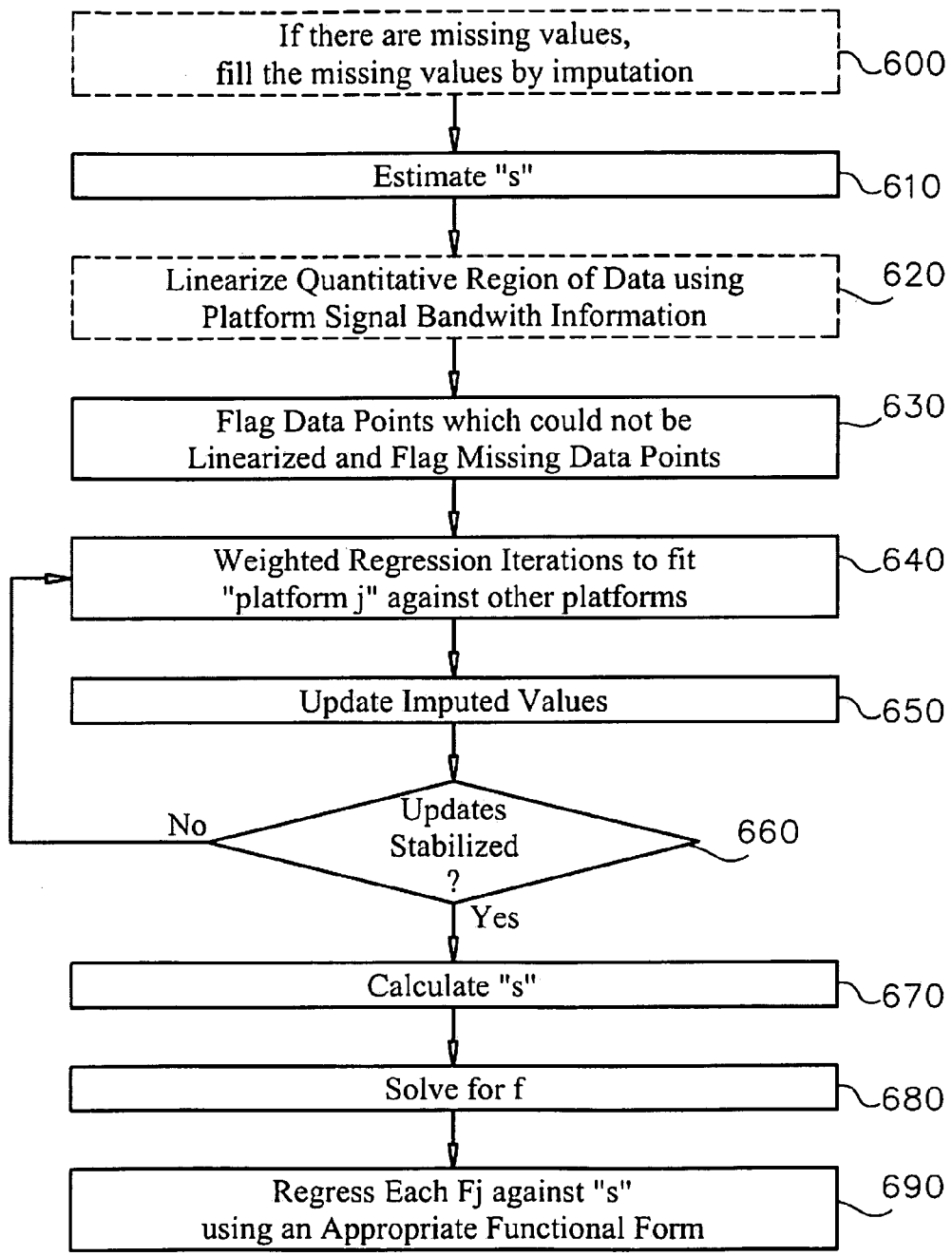
FIG. 6 is a flowchart showing steps that may be performed in creating conversion evaluations for cross-platform comparisons of data values as read by various platforms, according to the present invention.

FIG. 6 is a flowchart showing steps that may be performed in creating conversion evaluations for cross-platform comparisons of data values as read by various platforms. After loading the available data readings from the various platforms to be compared, if there are any missing values, then these values are filled at step 600 before calculating an estimate for "s" at step 610. By the current procedure, all values in the matrix generated, whether originally missing or non-missing, are provided viable consistent values in a simple, direct way involving minimal assumptions. Hence, for each specific platform the original non-missing assay values of all platforms are individually considered to estimate values for each specific platform by a series of univariate regressions using all possible platform pairings restricted within the quantitation ranges of both platforms with imputations restricted to non-missing signals of the x (regressor) platform within its quantitation range. The specific platform for which the missing values are being estimated is not excluded from this process, i.e., the specific platform is considered for application of univariate imputation regression, as an estimator of itself (auto-regression), to properly account for the possibility of region segments covered only by the specific platform itself. Optionally, the directional error methods can be used to impute values between platforms taken pair-wise. For each specific platform, all bivariate estimates of the profile values for that platform are combined to form an ensemble-estimated virtual profile. After processing each specific platform in this manner, the ensemble-estimated profiles are combined, one per platform, in a statistically meaningful manner, such as by averaging them and optionally weighting their estimated precision, or by the directional-error methods, for example, to provide a consistent estimate of "s" covering the total range defined by all samples.

At step 620, quantitative regions of data for each platform are selected and optionally linearized, assuming an appropriate functional form, such as the logistic dose-response function, for example, see http://www.graphpad.com/curvefit/introduction89.htm, using each platform's signal band width that is known. An example formula for optional linearization of the dose-response logistic is:

$$Ln[(max+d-signal)/(signal-min-d)]=b+m*c \qquad (6)$$

where
max=the saturation level signal;
d=tolerance for random error:
signal=platform scanner;
min=lowest concentration signal;
b=a locator for the concentration that creates a signal that is 50% between min and max;
m=the slope of ln signal versus ln concentration at b, which is a measure of sensitivity; and
c=ln(concentration of the analyte);
and where the dose-response curve is not flat (i.e., non-zero slope).

All data points that cannot be linearized, for whatever reason (e.g., not within signal bandwidth, signal bandwidth not provided for the platform providing data points, etc.) are flagged at step 630. Also, any remaining missing data points (missing values) are flagged in the positions of the chart/matrix where they should appear.

At step 640, platform j is fitted against all other platforms using weighted multivariate regression, to further improve the estimated profile of each platform, as follows:

$$SSQ_j = \sum_{k=1}^{m} \frac{(y_{jk} - f_{jk})^2}{\nabla f'_{jk} V \nabla f_{jk}} \qquad (7)$$

where
$SSQ_j$ is the resulting profile given by the multivariate regression;
m is equal to the number of platforms minus one (i.e., n−1);
y is the estimated platform signal derived from univariate regression;
$f$ is the multivariate model function;
$\nabla$ is the vector gradient operator; and
V is a diagonal variance matrix.

The total objective function is:

$$SSQ = \sum_{j=1}^{n} SSQ_j \qquad (8)$$

SSQ is a positive definite quadratic function of $f$ and its derivatives and hence, can be minimized. All weighted regressions of platforms are iterated until convergence, i.e., until SSQ achieves a minimum. The imputed values of the flagged data values are next updated (step 650), using the functionally extrapolated/interpolated values of the multivariate model. Only the missing data need be imputed.

At step 660, it is determined whether the [updated] imputed values have stabilized. Stabilization is characterized when the corrections to values to be made from one iteration to the next are insignificant (e.g., when they are comparable to numerical error). If it is determined that the imputed values have not yet stabilized, processing returns to step 640 to again perform the weighted regression iterations for fitting each platform (i.e., "platform j") to all other platforms. Then the imputed values are again updated at step 650 and again checked at step 660 to see whether they have stabilized. When it is determined at step 660 that the imputed data values have sufficiently stabilized, "s" is calculated at step 670 as follows:

$$s = \sum_{j=1}^{n} c_j f_j, c_j \geq 0, j=1, \ldots, n \qquad (9)$$

where
$c_j$ represents weighting factors that depend on platform error and quantitation strength, and which may be normalized. For example, $c_j$ may be inversely weighted by noise associated with $f_j$. Alternatively, $c_j$ may be set to one (1). For example, $$s = \sum_{j=1}^{n} f_j \nabla f'_j \cdot \nabla f_j \qquad (10)$$

using the gradient with respect to all other platforms. Given that both "y" values and "x" values have comparable error, one must reduce a directional error rather than the error only in the y-direction, which is assumed by regression theory.

Next, the function $f$ is solved for at step 680, by first initializing $f_j$ as $y_j$ (platform signals, j=1, . . . , n) to represent an ideal, error-free, perfect predictor, and initializing s as average of $y_j$. Note that in solving for s above, the solution gives a first approximation by iteration of the univariate methods used. Each $f_j$ is regressed against "s" at step 690, using an appropriate functional form such as a sigmoid as follows:

$$f_j = \min_j + \frac{\max_j - \min_j}{1 + \exp(-\beta_j[s - \alpha_j])} \qquad (11)$$

where β and α are logistic parameters of the four-parameter logistic dose-response function.

Where either or both of $\max_j$ and $\min_j$ can be predefined, or estimated, if supported by the data. Relative sensitivity between any two platforms j and k is defined by:

$$\frac{\partial f_j}{\partial s} \frac{\partial s}{\partial f_k} \qquad (12)$$

Hence, the present invention can convert from any given $f_j$ to any $f_k$ by first solving for "s" from $f_j$, and then solving for $f_k$ using the obtained solution for "s" using the respective sigmoid form factors for $f_j$ and $f_k$. The precision of any segment of "s" can be compared by calculating standard deviation within the segment for every platform that has at least three data points in the segment.

Figure 7:
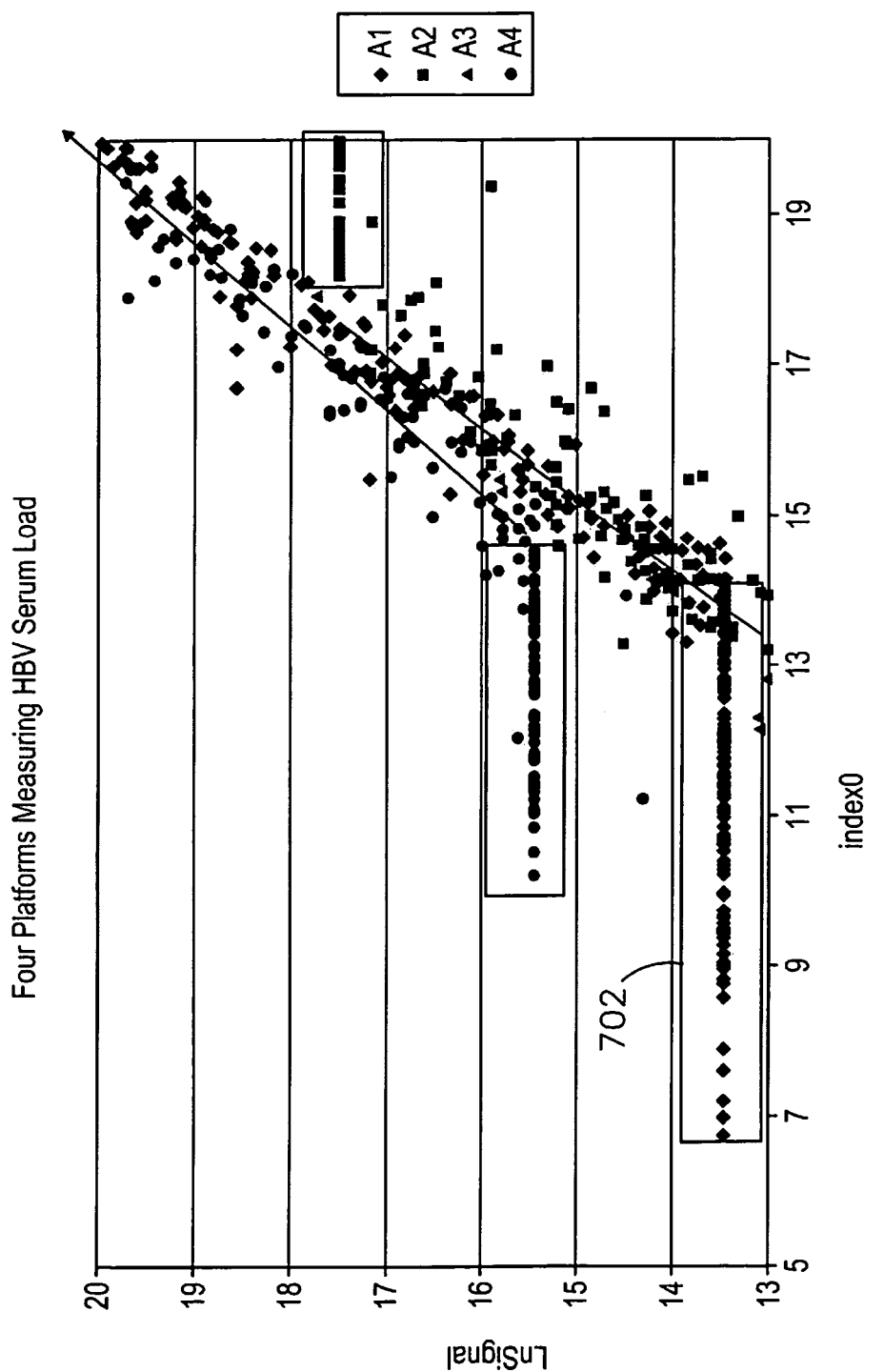
FIG. 7 shows a plot of initially ordered measurements taken by four platforms when measuring HBV serum load as the analyte.

FIG. 7 shows a plot of initially ordered measurements taken by four platforms when measuring HBV serum load as the analyte. The ln signal values are shown plotted against an initial index (index 0") resultant from an initial ordering process, such as discussed above (e.g., averaging, or the like). Also, if known bottle values are being measured, in addition to dilutions of these known bottle values, this adds leverage to the initial ordering process, as the relative order of a known bottle sample and its diluents is known. FIG. 7 clearly illustrates the regions in which the platforms lose the ability to detect low quantities/concentrations of analyte (e.g., see 702 with regard to platform and 704 with regard to platform A4) and a region 706 in which platform A2 has become saturated. These initially ordered values are used to replace the values in regions where the platforms cannot detect low concentrations, the values in the saturation regions, and any missing values, by employing the techniques described above.

Figure 8:
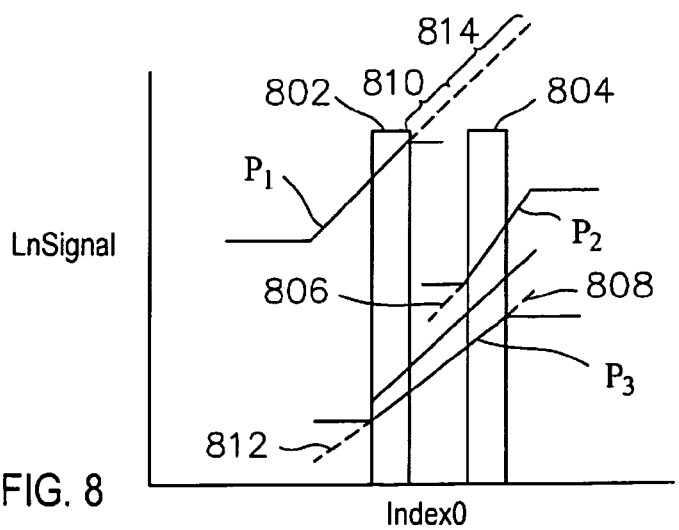
FIG. 8 schematically illustrates plots of three platform signals against an initial index 0 for purposes of explanation of the formation of virtual platforms.

FIG. 8 schematically illustrates plots of three platform signals against index 0 for purposes of explanation of the formations of virtual platforms. Rectangular box 802 identifies index values where plots P1 and P3 overlap and rectangular box 804 identifies index values where plots P2 and P3 overlap. Note that in this example there is no multivariate overlap of index values for quantitations that are reliable (i.e., not in the saturation segment or the segment where concentrations are too low to get a reliable reading).

By applying the univariate regression techniques described above, virtual profiles for each platform may be developed. For example, the overlapping values in rectangle 804 may be used to develop a relationship between the values of P2 within 804, relative to the values of P3 within 804. By univariate regression, the values of P2 within 804 may regressed against the values of P3 within 804 to develop a first or second order relationship that characterizes a value in P2 with respect to a value of P3, given the same index value. Using this relationship, the values of P2 which are unreliable since the concentration of the analyte is too low to get a detectable reading, can be replaced by values based on the relationship derived between P2 and P3, thereby extending the reliable values for P2, as shown by dotted segment 806.

Similarly, by univariate regression, the values of P3 within 804 may be regressed against the values of P2 within 804 to develop a first or second order relationship that characterizes a value in P3 with respect to a value of P2, given the same index value. Using this relationship, the values of P3 which are saturated can be replaced by values based on the relationship derived between P3 and P2, thereby extending the reliable values for P3, as shown by dotted segment 808. Further iterations of univariate regression may be carried out between values of P1 and P3 within rectangle 802 to determine segment 810, and between values of P3 and P1 within rectangle 802 to determine segment 812. Note that univariate regression iterations may be continued to further extend the virtual profiles based on newly developed overlapping values from previous iterations. For example, the overlapping values of 802 may be regressed with those of 806 to formulate a relationship used to extend profile P1 based on the relationship with P2, as shown at 814. Univariate regression iterations may be continued until all profiles span the range of all measured samples. All extended profiles must be quantitative, e.g., linearly proportional to analyte concentration. The virtual profiles may then be combined to create the super virtual profile described above. As described previously, super virtual profiles can be merged across major data gaps.

In the example shown in FIG. 8, there are no gaps between the profiles (i.e., no index values for which there is not at least one reliable LnSignal value). In situations where there is one or more gaps in the data, however, multiple partial super virtual platforms are created in the manner described above with regard to the creation of a super virtual platform, wherein one partial super virtual platform is created for each group of data having no gaps, and then the multiple partial super virtual platforms are joined (effectively "crossing the major gaps") by merging the partial super virtual platforms to form a single super virtual platform.

Figure 9:
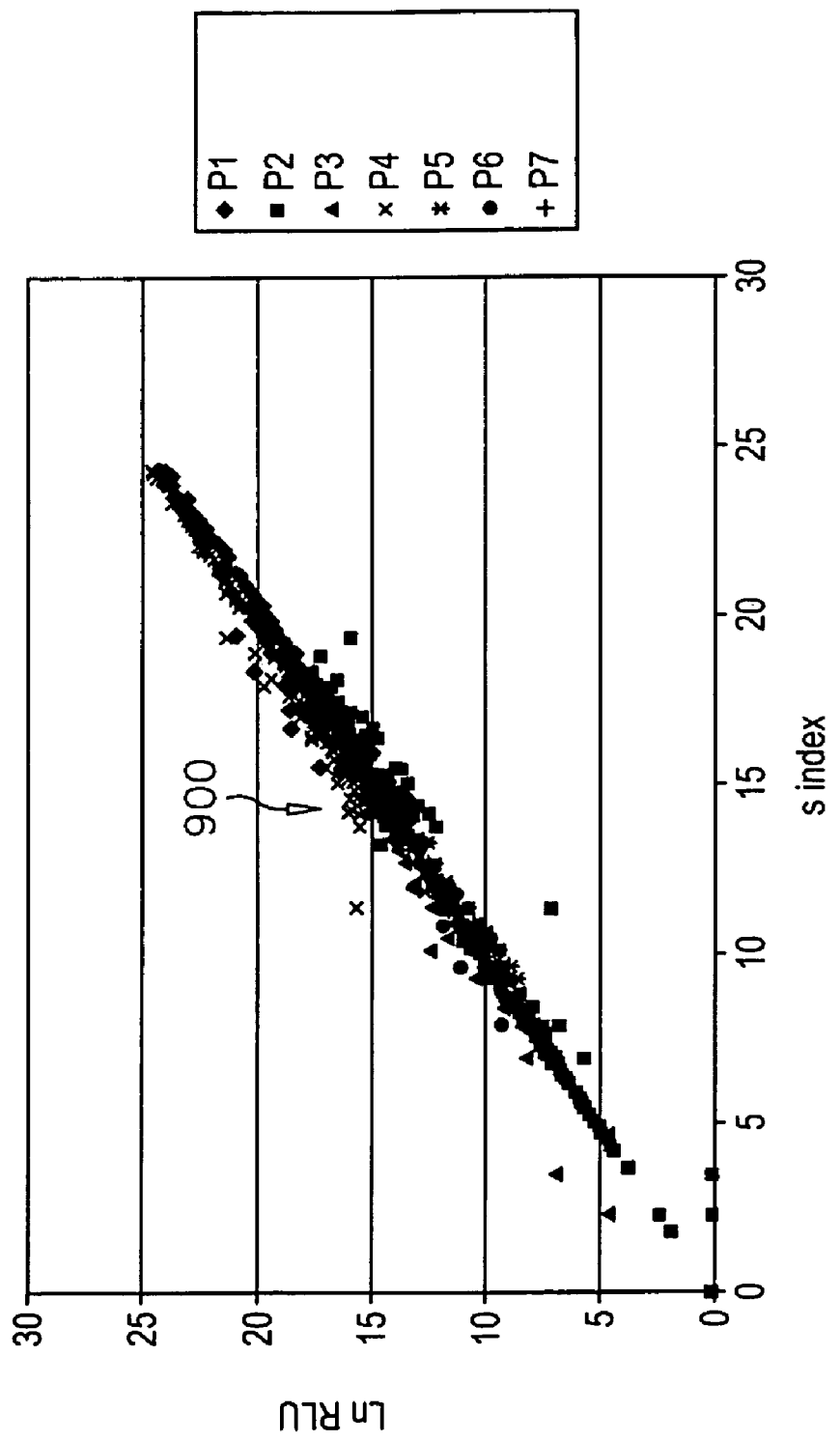
FIG. 9 shows a plot of seven different platform readings after application of the super virtual platform ("s index") to correlate the measurements.

FIG. 9 shows a plot of seven different platform readings after application of the super virtual platform ("s index") to correlate the measurements via one iteration. The signal readings are plotted as Ln RLU (relative luminosity units) versus "s". As noted above, variations in slope of the plots indicate varying sensitivity, wherein a higher relative slope represents higher relative sensitivity, and scatter of the plotted points about the plotted linearization of a platform plot is representative of precision, wherein a relatively greater distance of deviation from the linear plot represents relatively lesser precision.

Preferred embodiments of the present invention make certain assumptions about the methods being analyzed and the data input to the techniques of this invention. That is, certain criteria must be met in order for the normalizing procedures of this invention to work. These assumptions are the following.

First, multiple measurement methods for assessing the same physical property must be compared together. The techniques of this invention do not act on just one method. Obviously, two mechanistically different assays for quantifying HBV DNA meet this criterion. However, the range of methods that qualify is broader than this. For example, because a given assay may behave slightly differently when conducted under slightly different conditions, a single assay when conducted under these slightly different conditions may form the basis of two or more independent methods which can be employed with the multi-measurement technique of this invention. For example, one company's HBV DNA assay may be performed with two different standards or on two different assay plates to provide two distinct methods as required to meet this criterion.

Second, for each method, the number and distribution of data points (measured values for samples under consideration) is adequate to fully determine each of the parameters required to specify the assumed form of the response curves (e.g., two unique x points for a line (slope and intercept), three unique x points for a quadratic curve, etc.). The minimum total of all properly distributed data required to handle all measurement methods in the normalization is the sum of the number of parameters for each method curve plus the number of samples to be corrected used to generate the data plus one (for an anchor x value). This additional requirement is imposed by correction factors for all samples except one (designated as the anchor value). As explained, these correction factors are provided to allow adjustment of the relative position of the sample values but they are additional parameters that must be solved for.

Third, each individual measurement method has the property of reasonable continuity or smoothness as the hidden phenomena varies. In addition, the response curves must be monotonic and non-constant. Thus, it can not have two values of the underlying property for any one measured value (i.e., a one-to-one mapping between measured value and underlying property is required).

Figure 10:
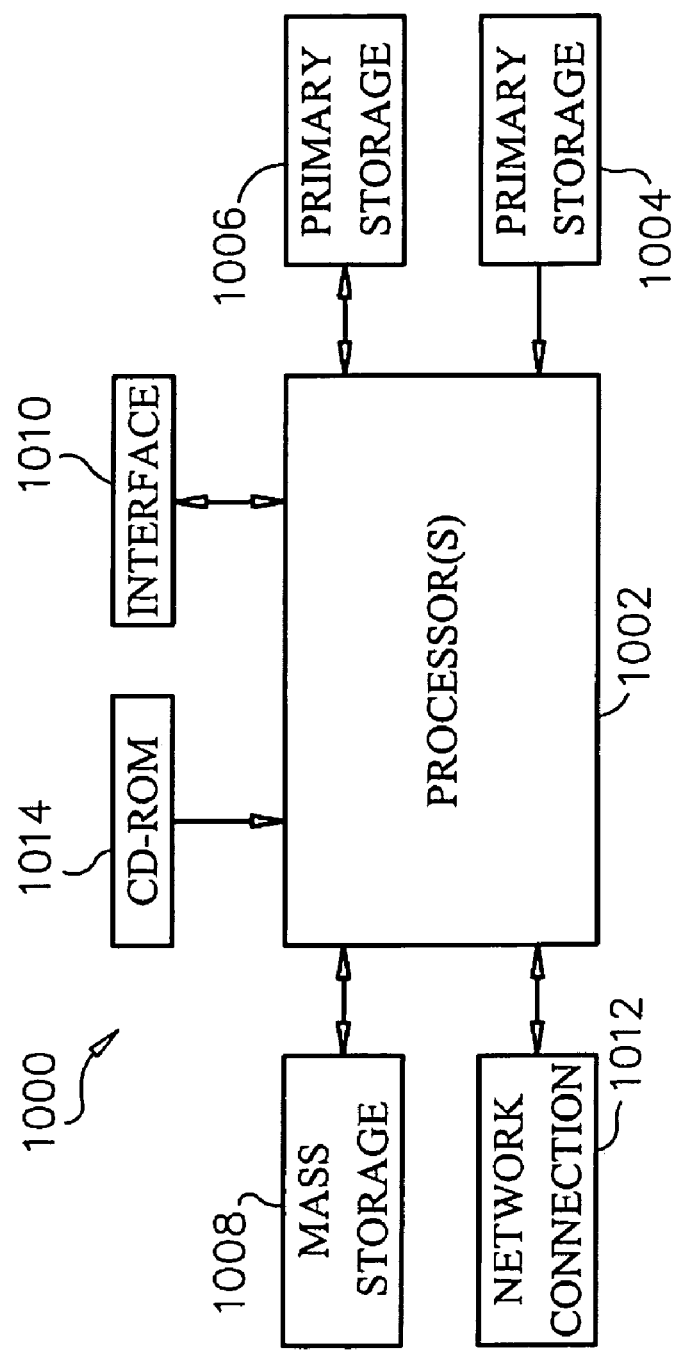
FIG. 10 illustrates a typical computer system that may be employed in accordance with the present invention.

FIG. 10 illustrates a typical computer system in accordance with an embodiment of the present invention. The computer system 1000 includes any number of processors 1002 (also referred to as central processing units, or CPUs) that are coupled to storage devices including primary storage 1006 (typically a random access memory, or RAM), primary storage 1004 (typically a read only memory, or ROM). As is well known in the art, primary storage 1004 acts to transfer data and instructions uni-directionally to the CPU and primary storage 1006 is used typically to transfer data and instructions in a bi-directional manner Both of these primary storage devices may include any suitable computer-readable media such as those described above. A mass storage device 1008 is also coupled bi-directionally to CPU 1002 and provides additional data storage capacity and may include any of the computer-readable media described above. Mass storage device 1008 may be used to store programs, data and the like and is typically a secondary storage medium such as a hard disk that is slower than primary storage. It will be appreciated that the information retained within the mass storage device 1008, may, in appropriate cases, be incorporated in standard fashion as part of primary storage 1006 as virtual memory. A specific mass storage device such as a CD-ROM 1014 may also pass data uni-directionally to the CPU.

CPU 1002 is also coupled to an interface 1010 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1002 optionally may be coupled to a computer or telecommunications network using a network connection as shown generally at 1012. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for multivariate regression may be stored on mass storage device 1008 or 1014 and executed on CPU 1008 in conjunction with primary memory 1006.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of correlating measurements of the same group of properties taken by different platforms, said method comprising the steps of:

representing measurement values of each platform as a vector, respectively, wherein a position of each measurement value in a vector corresponds to the same position in all other vectors and measures the same property;

calculating a virtual platform with corresponding value positions containing ensemble values representative of the measurement values in all platform vectors at the corresponding positions;

constructing surrogate values to represent the true values of the properties being measured, to provide consensus-correct ordering of the platform vectors;

ordering and scaling the ensemble values in the virtual platform;

for each of the platforms, assuming a mathematical form of a response curve describing the surrogate values as a function of the properties being measured; and simultaneously solving for a correction factor for at least one surrogate value with regard to at least one platform.

2. The method of claim 1, wherein said surrogate values, s are functionally related to the measured values of each platform as follows:

$$s = \sum_{j=1}^{n} c_j f_j, c_j \geq 0, j = 1, \ldots, n,$$

such that for a given value of s, all platforms ($f_j$,j=1, . . . , n) have a unique value and is a monotonic, non-constant function of s.

3. The method of claim 1, wherein at least one of the measurement values in at least one of the platform vectors is missing or invalid, said method further comprising imputing a value for each said missing or invalid measurement value and inserting the imputed value in a position in which said at least one missing or invalid measurement value occurs, respectively.

4. The method of claim 3, wherein said imputing is performed by at least one of manually imputing and performing a series of univariate regressions.

5. The method of claim 3, wherein the imputed values comprise most-likely expected values.

6. A method of correlating measurements of the same group of properties taken by different platforms, said method comprising the steps of:

representing measurement values of each platform as a vector, respectively, wherein a position of each measurement value in a vector corresponds to the same position in all other vectors and measures the same property;

calculating a virtual platform with corresponding value positions containing ensemble values representative of the measurement values in all platform vectors at the corresponding positions; and ordering and scaling the ensemble values in the virtual platform; wherein at least one of the measurement values in at least one of the platform vectors is missing or invalid, and wherein most-likely expected values are inserted in positions in which said at least one missing or invalid measurement value occurs, respectively, and wherein said most-likely expected values are determined by at least one of manually imputing and performing a series of univariate regressions.

7. A method comprising forwarding a result obtained from the method of claim 6 to a remote location.

8. A method comprising transmitting data representing a result obtained from the method of claim 6 to a remote location.

9. A method comprising receiving a result obtained from a method of claim 6 from a remote location.

* * * * *

UNITED STATES PATENT AND TRADEMARK OFFICE
CERTIFICATE OF CORRECTION

PATENT NO.       : 7,072,806 B2                                         Page 1 of 1
APPLICATION NO.  : 11/169991
DATED            : July 4, 2006
INVENTOR(S)      : Minor It is certified that error appears in the above-identified patent and that said Letters Patent is hereby corrected as shown below:

On the Title page, item (56), under "Other Publications", in column 1, line 5, after "downloaded" insert -- , --.

On the Title page, item (56), under "Other Publications", in column 2, line 7, after "downloaded" insert -- , --.

Signed and Sealed this

Twelfth Day of December, 2006

JON W. DUDAS
*Director of the United States Patent and Trademark Office*